United States Patent [19]

Hatono et al.

[11] Patent Number: 4,793,948
[45] Date of Patent: Dec. 27, 1988

[54] BILE ACID DERIVATIVES AND PRODUCTION THEREOF

[75] Inventors: Shunsou Hatono; Akira Yazaki; Susumu Yoshida, all of Hiroshima, Japan

[73] Assignee: Wakunaga Seiyaku Kabushiki Kaisha, Osaka, Japan

[21] Appl. No.: 7,663

[22] Filed: Jan. 28, 1987

[30] Foreign Application Priority Data

Jan. 28, 1986 [JP] Japan .................................. 61-16458

[51] Int. Cl.⁴ .............................................. C07J 1/00
[52] U.S. Cl. .................................................. 260/397.1
[58] Field of Search ..................................... 260/397.1

[56] References Cited

FOREIGN PATENT DOCUMENTS 66924 10/1978 Romania .......................... 260/397.1

OTHER PUBLICATIONS

Chemical Abstracts; vol. 103 (1985)#134470G; Baracu et al.
Chemical Abstracts; vol. 98 (1983)#179757A; Niculescu-Duvaz et al.
Chemical Abstracts; vol. 91 (1979)#211670K; Niculescu-Duvaz et al.
Chemical Abstracts; vol. 78 (1973)#136513N; Wolf et al.

Primary Examiner—Leonard Schenkman
Assistant Examiner—Joseph A. Lipovsky
Attorney, Agent, or Firm—Oblon, Fisher, Spivak, McClelland & Maier

[57] ABSTRACT

A bile acid derivative having carcinostatic activity represented by the following formula (1):

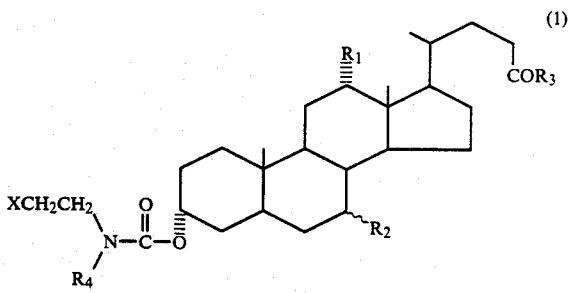

wherein each of $R_1$ and $R_2$ is a hydrogen atom or a hydroxyl group, $R_3$ is a hydroxyl group, benzyloxy group or $-(NH-CH_2)_n R_5$ (wherein $R_5$ is a carboxyl group or sulfonyl group, and n represents the integer of 1 or 2), X is a halogen atom, $R_4$ is a hydrogen atom or $XCH_2CH_2-$, ⫼⫼⫼is an α-bond, and ⁓ is an α- or β-bond is produced by the steps (a) and (b), the steps (a) and (c), or the steps (a), (b), (c) and (d) described below:

(a) causing an active carbonation reagent to react with a bile acid derivative wherein the carboxyl group is esterified;

(b) causing an aminoalkylhalide to react with the active carbonated product obtained;

(c) subjecting the bile acid derivative obtained in the above steps (a) and (b) to hydrolysis; and (d) causing the above hydrolyzate to react with an aminoalkyl derivative in the presence of a condensing agent.

6 Claims, No Drawings

BILE ACID DERIVATIVES AND PRODUCTION THEREOF

BACKGROUND OF THE INVENTION

This invention relates to novel bile acid derivatives and production thereof. These bile acid derivatives are useful as therapeutical drugs for cancers.

Bile acids are one kind of steroid compounds, constituting the main components of bile of vertebrate animals. Most of these bile acids have been known to be generally hydroxylated derivatives of 5β-cholanic acid having 24 carbon atoms.

In human bile, cholic acid, deoxycholic acid, chenodeoxycholic acid, lithocholic acid and the like are contained, but slight differences can be seen in the kind and composition of the bile acids depending on the species of animals (for example, there exist species specific bile acids such as ursodeoxycholic acid in the bile of bear and β-muricholic acid in the bile of rat).

These bile acids are essential components absolutely required for absorption of fats or vitamins and control of lipid metabolism in living bodies, and among them, dehydrocholic acid and ursodeoxycholic acid have been frequently used for the purpose of promoting bile secretion, dissolution of gallstone, lipid digestion and absorption, conditioning of intesting, etc.

On the other hand, as for the distribution of bile acids, they are synthesized from cholesterol in the liver and, after being conjugated with glycine or taurine, secreted into the bile and stored and concentrated within the gallbladder, and thereafter released into the duodenum. Bile acids have been known to be absorbed through the ileum after having fullfilled functions such as emulsification (solubilization) of substances insoluble in water in the small intestine, enter the portal vein, be taken up in the liver cells and again secreted into the bile (circulation of intestine-portal vein-liver-bile duct, namely, enterohepatic circulation).

Recently, studies have been made on the derivatives utilizing the unique functions possessed by the bile acids as described above. For example, Ito et al. synthesized compounds in which iminodiacetic acid is bound to the 23-position carboxyl group of naturally occurring bile acids, and reported that they are useful as gallstone dissolving agents on the basis of the finding that they have a remarkable calcium carbonate dissolving activity (see Japanese Patent Laid-Open Publications Nos. 161996/1985 and 163896/1985). However, concerning the derivatives in which N-haloalkylcarbamoyl group is bound to the 3-position group of naturally occurring bile acids, they have not even existed themselves, let alone has there been any report up to date about the fact that carcinostatic activity is found in the natural bile acids or their derivatives.

SUMMARY OF THE INVENTION

This invention is concerned with the bile acid derivatives having an N-haloalkylcarbamoyl group bound to the 3-position hydroxyl group of bile acids and their salts.

More particularly, the bile acid derivatives according to the present invention are represented by the following formula (1):

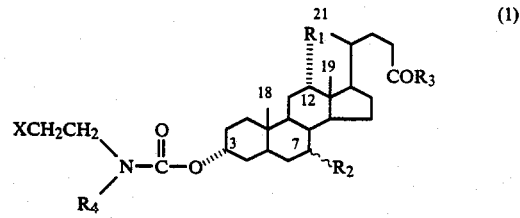

wherein each of $R_1$ and $R_2$ is a hydrogen atom or a hydroxyl group, $R_3$ is a hydroxyl group, lower alkoxyl group, benzyloxyl group or $-NH-(CH_2)_n R_5$ (wherein $R_5$ is a carboxyl group or sulfonyl group, and n represents the integer of 1 or 2), X is a halogen atom, $R_4$ is a hydrogen atom or $XCH_2CH_2-$, ⁞⁞⁞⁞⁞ is an α-bond, and ∼∼∼ is an α- or β-bond.

Further, the process for producing the bile acid derivatives of the above formula (1) according to the present invention comprises the following steps (a) and (b), the steps (a), (b) and (c), or the steps (a), (b), (c) and (d):

(a) causing an active carbonation reagent to react with a bile acid derivative represented by the formula (2):

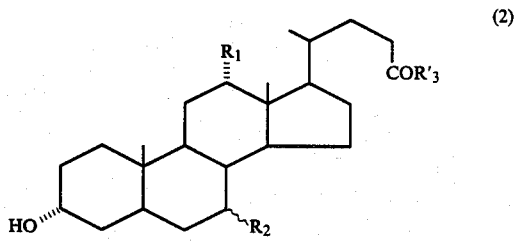

wherein each of $R_1$ and $R_2$ is a hydrogen atom or a hydroxyl group, $R'_3$ is a lower alkoxyl group or benzyloxyl group, ⁞⁞⁞⁞⁞ is an α-bond, and ∼∼∼ is an α- or β-bond;

(b) causing a compound represented by the formula (3):

wherein X is a halogen atom, and $R_4$ is a hydrogen atom or $XCH_2CH_2-$, to react with the active carbonated product obtained;

(c) subjecting the bile acid derivative obtained in the above steps (a) and (b) to hydrolysis; and (d) causing the above hydrolyzate to react with a compound represented by the formula (4):

$$H_2N-(CH_2)_n R_5 \quad (4)$$

wherein $R_5$ is a carboxyl group or sulfonyl group, and n represents the integer of 1 or 2, in the presence of a condensing agent.

The bile acid derivatives and their salts according to the present invention are expected to contribute greatly to cancer disease countermeasures, particularly therapy and prophylaxis of liver-bile duct system cancer diseases, partly because enterohepatic circulation may be predicted since they are derived from naturally occurring bile acids (e.g., cholic acid, deoxycholic acid, ursodeoxycholic acid, chenodeoxycholic acid and lithocholic acid) and partly because they have per se carcinostatic activity.

DETAILED DESCRIPTION OF THE INVENTION

Bile Acid Derivatives

Properties

The bile acid derivatives according to the present invention are represented by the above formula (1). The definitions of the symbols in the formula are also as defined above. The lower alkoxy group of $R_3$ ordinarily has about 1 to 4 carbon atoms. Two Xs which will exist when $R_4$ is $XCH_2CH_2-$ can be different.

Furthermore, "their salts" refer to salts with alkali metals or alkaline earth metals such as sodium, potassium and magnesium, or salts with any of pharmaceutically acceptable bases such as ammonium salts and amine salts.

Specific examples of the compounds are shown together with the physical and chemical properties thereof in the following Table 1.

TABLE 1

| Compound | | $R_1$ | $R_2$ | $R_3$ | $R_4$ | X | 18-CH₃ | 19-CH₃ | 21-CH₃ | 3-H | 7-H | 12-H | $R_3$ | $-\overset{O}{\underset{\|}{C}}-N\overset{CH_2CH_2X}{\underset{R_4}{}}$ | ¹³C—NMR $-N-\overset{O}{\underset{\|}{C}}-O$ |
|---|---|---|---|---|---|---|---|---|---|---|---|---|---|---|---|
| 1 | CA—Me—NM | —OH | α-OH | —OCH₃ | CH₂CH₂Cl | Cl | 0.69 | 0.90 | 0.97 | 4.49 | 3.85 | 3.99 | 3.66(3H, s) | 3.53~3.73(8H, m) | 155.6 |
| 2 | CA—Et—NM | —OH | α-OH | —OCH₂CH₃ | CH₂CH₂Cl | Cl | 0.70 | 0.91 | 0.98 | 4.50 | 3.85 | 3.99 | 1.25(3H, t, J=7Hz) 4.12(2H, q, J=7Hz) | 3.53~3.74(8H, m) | 155.6 |
| 3 | CA—Bz—NM | —OH | α-OH | —OCH₂Ph | CH₂CH₂Cl | Cl | 0.67 | 0.91 | 0.97 | 4.50 | 3.86 | 3.98 | 5.11ᵇ(2H) 7.30~7.40(5H, m) | 3.55~3.73(8H, m) | 155.6 |
| 4 | CA—Bz—NM | —OH | H | —OCH₃ | CH₂CH₂Cl | Cl | 0.68 | 0.91 | 0.98 | 4.63 | | 3.99 | 3.66(3H, s) | 3.54~3.76(8H, m) | 155.6 |
| 5 | DCA—Me—NM | H | β-OH | —OCH₂Ph | CH₂CH₂Cl | Cl | 0.66 | 0.95 | 0.92 | 4.60 | ᵃ | | 5.10ᵇ(2H) 7.30~7.40(5H, m) | 3.53~3.74(9H, m) | 155.4 |
| 6 | UDCA—Bz—NM | H | α-OH | —OCH₂Ph | CH₂CH₂Cl | Cl | 0.64 | 0.91 | 0.92 | 4.51 | 3.86 | | 7.30~7.40(5H, m) 5.11ᵇ(2H) | 3.55~3.73(8H, m) | 155.6 |
| 7 | CDCA—Bz—NM | H | H | —OCH₂Ph | CH₂CH₂Cl | Cl | 0.63 | 0.91 | 0.92 | 4.64 | | | 7.30~7.40(5H, m) 5.10ᵇ(2H) | 3.55~3.73(8H, m) | 155.5 |
| 8 | LCA—Bz—NM | —OH | α-OH | —OCH₂Ph | H | Cl | 0.66 | 0.90 | 0.97 | 4.46 | 3.84 | 3.96 | 5.11ᵇ(2H) 7.30~7.40(5H, m) | 3.48ᶜ(2H), 3.58ᵈ(2H) 5.31ᵉ(1H) | 156.3 |
| 9 | CA—Bz—CEA | —OH | H | —OCH₂Ph | H | Cl | 0.65 | 0.91 | 0.96 | 4.60 | | 3.97 | 5.11ᵇ(2H) 7.30~7.40(5H, m) | 3.49ᶜ(2H), 3.59ᵈ(2H) 5.18ᵉ(1H) | 156.1 |
| 10 | DCA—Bz—CEA | H | β-OH | —OCH₂Ph | H | Cl | 0.66 | 0.95 | 0.92 | 4.57 | ᵃ | | 5.11ᵇ(2H) 7.30~7.40(5H, m) | 3.50ᶜ(2H), 3.59ᵈ(3H) 5.20ᵉ(1H) | 156.0 |
| 11 | UDCA—Bz—CEA | —OH | H | —OCH₂Ph | H | Br | 0.65 | 0.91 | 0.96 | 4.60 | 3.87 | 3.97 | 5.11ᵇ(2H) 7.30~7.40(5H, m) | 3.44ᵈ(2H), 3.54ᶜ(2H) 5.16ᵉ(1H) | 156.1 |
| 12 | DCA—Bz—BEA | H | β-OH | —OCH₂Ph | H | Br | 0.65 | 0.95 | 0.92 | 4.56 | ᵃ | | 5.10ᵇ(2H) 7.30~7.40(5H, m) | 3.43ᵈ(2H), 3.52ᶜ(3H) 5.49ᵉ(1H) | 156.0 |
| 13 | UDCA—Bz—BEA | —OH | α-OH | —OCH₂Ph | CH₂CH₂Br | Br | 0.66 | 0.89 | 0.96 | 4.48 | 3.83 | 3.96 | 5.11ᵇ(2H) 7.30~7.40(5H, m) | 3.42ᶜ(4H) 3.57-3.67(4H, m) | 155.2 |
| 14 | CA—Bz—BBEA | —OH | α-OH | OH | CH₂CH₂Cl | Cl | 0.71 | 0.91 | 0.99 | 4.51 | 3.87 | 4.01 | | 3.56~3.73(8H, m) | 155.6 |
| 15 | CA—NM | —OH | H | OH | CH₂CH₂Cl | Cl | 0.69 | 0.92 | 0.99 | 4.64 | | 4.01 | | 3.55~3.76(8H, m) | 155.6 |
| 16 | DCA—NM | H | β-OH | OH | CH₂CH₂Cl | Cl | 0.69 | 0.96 | 0.94 | 4.60 | ᵃ | | | 3.52~3.73(9H, m) | 155.5 |
| 17 | UDCA—NM | H | α-OH | OH | CH₂CH₂Cl | Cl | 0.67 | 0.92 | 0.94 | 4.51 | 3.87 | | | 3.54~3.73(8H, m) | 155.6 |
| 18 | CDCA—NM | H | H | OH | CH₂CH₂Cl | Cl | 0.66 | 0.93 | 0.92 | 4.65 | | | | 3.57~3.74(8H, m) | 155.6 |
| 19 | LCA—NM | —OH | α-OH | OH | H | Cl | 0.70 | 0.91 | 0.99 | 4.47 | 3.87 | 4.01 | | 3.50ᶜ(2H), 3.59ᵈ(2H) 3.39ᵉ(1H) | 156.5 |
| 20 | CA—CEA | —OH | H | OH | H | Cl | 0.68 | 0.92 | 0.98 | 4.61 | | 4.00 | | 3.51ᶜ(2H), 3.60ᵈ(2H) 5.19ᵉ(1H) | 156.3 |
| 21 | DCA—CEA | H | β-OH | OH | H | Cl | 0.68 | 0.96 | 0.94 | 4.57 | ᵃ | | | 3.51ᶜ(2H), 3.60ᵈ(3H) 5.20ᵉ(1H) | 156.1 |
| 22 | UDCA—CEA | —OH | H | OH | H | Br | 0.68 | 0.91 | 0.98 | 4.61 | 3.87 | 4.01 | | 3.45ᵈ(2H), 3.56ᶜ(2H) 5.38ᵉ(1H) | 156.3 |
| 23 | DCA—BEA | H | β-OH | OH | H | Br | 0.68 | 0.96 | 0.94 | 4.57 | ᵃ | | | 3.46ᵈ(2H), 3.56ᶜ(3H) 5.20ᵉ(1H) | 156.0 |
| 24 | UDCA—BEA | | | | | | | | | | | | | | |

TABLE 1-continued $^1$H—NMR(1~24: CDCl$_3$, 25~28: d$_5$-Pyridine)

| Compound | R$_1$ | R$_2$ | R$_3$ | R$_4$ | X | 18-CH$_3$ | 19-CH$_3$ | 21-CH$_3$ | 3-H | 7-H | 12-H | R$_3$ | $-\overset{O}{\overset{\|}{C}}-N\overset{CH_2CH_2X}{\underset{R_4}{\diagdown}}$ | $^{13}$C—NMR $N-\overset{O}{\overset{\|}{C*}}-O$ |
|---|---|---|---|---|---|---|---|---|---|---|---|---|---|---|
| 24 CA—BBEA | —OH | α-OH | OH | CH$_2$CH$_2$Br | Br | 0.70 | 0.90 | 0.99 | 4.49 | 3.87 | 4.00 | | 3.44$^f$(4H) 3.59~3.69(4H, m) | 155.4 |
| 25 CA—TAU—NM | —OH | α-OH | NHCH$_2$CH$_2$SO$_3$H | CH$_2$CH$_2$Cl | Br | 0.75 | 0.94 | 1.15 | 4.70 | 4.04 | $^a$ | 3.53(2H, t, J=7Hz) 4.17~4.28(2H, m) 5.81$^c$(1H) | 3.45~3.66(4H, m) 3.67~3.87(4H, m) | 155.9 |
| 26 CA—Gly—NM | —OH | α-OH | NHCH$_2$COOH | CH$_2$CH$_2$Cl | Cl | 0.77 | 0.94 | 1.17 | 4.70 | 4.03 | 4.22 | 4.47(2H, d, J=5.5) 8.85$^c$(1H) | 3.41~3.52(2H, m) 3.52~3.64(2H, m) 3.64~3.86(4H, m) | 155.8 |
| 27 CA—Gly—CEA | —OH | α-OH | NHCH$_2$COOH | H | Cl | 0.77 | 0.93 | 1.19 | 4.77 | 4.03 | 4.21 | 4.49(2H, d, J=6) 8.86$^c$(1H) | 3.56~3.70(2H, m) 3.70~3.79(2H, m) 7.79$^c$(1H) | 157.2 |
| 28 CA—Gly—BEA | —OH | α-OH | NHCH$_2$COOH | H | Br | 0.77 | 0.93 | 1.19 | 4.76 | 4.03 | 4.21 | 4.48(2H, d, J=6) 8.89$^c$(1H) | 3.54~3.65(2H, m) 3.65~3.79(2H, m) 7.82$^c$(1H) | 157.1 |

$^a$undetectable because of overlapping with other signals;
$^b$split to J=12.5 Hz due to asymmetry; center value is shown;
$^c$broad triplet-like split; J=5-6;
$^d$broad quintet-like split; J=5-6;
$^e$broad triplet-like split; J=6.5;
$^f$broad triplet-like split; J=4.5

Utility

The bile acid derivatives according to the present invention have carcinostatic activity to the same extent as the already existing carcinostatic agents and yet are of low toxicity.

Accordingly, these compounds can be used as carcinostatic agents (for details, see the description given hereinafter).

Production of the Bile Acid Derivatives

The bile acid derivatives of the formula (1) according to the present invention can be produced according to any desired method suited for the purpose.

Preferable examples of such method comprise practicing the steps (a) and (b) as described above successively, and, if necessary, up to the step (c), or (d).

In these examples, the compounds of the formula (2) are used as the starting materials, and the group $R_3'$ in the formula (2) is the same as the group $R_3$ of the formula (1) except that a hydroxyl group and $-N(H-CH_2)_{\overline{n}}R_5$ are contained. That is, in these examples, the hydroxyl group and $-NH-(-CH_2)_{\overline{n}}R_5$ of the group $R_3$ are introduced later (respectively in steps (c) and (d)). However, as long as the compounds of the formula (1) can be obtained, any other reactions or steps can be utilized as a matter of course.

The steps in these preferable examples will now be described in detail below.

Step (a)

For example, an alkali salt of a natural bile acid selected from cholic acid, deoxycholic acid, ursodeoxycholic acid, chenodeoxycholic acid and lithocholic acid is allowed to react with a lower alkyl halide having 1 to 4 carbon atoms such as methyl iodide, methyl bromide, methyl chloride, ethyl iodide, ethyl bromide, isopropyl iodide or butyl bromide, or a benzyl halide such as benzyl chloride or benzyl bromide in a conventional manner, and the alkyl ester of bile acid obtained (the compound of the above formula (2) in which $R_3'$ is a lower alkoxy group or benzyloxyl group) is used as the starting reactant. This reactant is allowed to react with an active carbonation reagent (referring to a divalent reagent having active groups such as halogen atoms, succinimidyloxyl groups or benzotriazole groups on both ends of the carbonyl groups thereof) such as carbonyl dihalide, N,N'-disuccinimidylcarbonate and chlorocarbonylbenzotriazole in a solvent having no reactive hydrogen atom such as ethyl acetate, chloroform, methylene chloride, benzene or acetone, or in a mixture thereof, whereby an active carbonated product [the above starting reactant (the alkyl ester of bile acid) having the above active carbonation reagent condensed onto its 3-position hydroxyl group] can be obtained.

In the above active carbonation reaction, acidic substances such as hydrogen halide and N-hydroxysuccinimide may be frequently formed as by-products to interfere with the reaction. In such a case, it is possible to add in advance in the reaction system an inorganic salt such as sodium carbonate, potassium carbonate or sodium hydrogencarbonate, or a tertiary amine such as pyridine or triethylamine to neutralize successively the above by-products formed.

Step (b)

The above active carbonated product can be allowed to react with a compound represented by the above formula (3), in which the definitions of the symbols are as defined above, (this compound is a known substance and may be synthesized according to any desired method, or a commercially available reagent may be used) or its salt (salt with any desired acidic substance such as hydrochloric acid, sulfuric acid or acetic acid) in the presence of an inorganic salt such as sodium carbonate, potassium carbonate or sodium hydrogencarbonate, or a tertiary amine such as pyridine or triethylamine in a solvent having no reactive hydrogen atom similarly as in step (a) above to obtain a compound of the above formula (1) in which $R_3$ is a lower alkoxy group or benzyloxyl group.

Step (c)

Further, the thus-obtained compound can be subjected to hydrolysis in an organic solvent miscible with water such as dioxane, tetrahydrofuran or a $C_1-C_4$ lower alcohol, or a solvent comprising a mixture of these and an appropriate amount of water in the presence of any desired inorganic or organic acid catalyst such as hydrochloric acid, acetic acid, sulfuric acid, p-toluenesulfonic acid, trifluoroacetic acid, trifluoromethane sulfonic acid, tartaric acid, succinic acid or citric acid, or a base catalyst selected from an inorganic salt such as sodium hydroxide, sodium carbonate, potassium carbonate or sodium hydrogencarbonate, or a quaternary ammonium hydroxide such as tetraethylammonium hydroxide to obtain a compound of the above formula (1) wherein $R_3$ is a hydrogen atom.

In the case of the compound of the above formula (1) wherein $R_3$ is a benzyloxy group, it is possible to convert the $R_3$ group to a hydroxyl group by a reaction with a catalyst for hydrogenation such as palladium or platinum under a hydrogen atmosphere in an organic solvent such as tetrahydrofuran, ethyl acetate or a $C_1-C_4$ lower alcohol.

Step (d)

The compound obtained in the steps as described above can be subsequently subjected to the reaction with the compound of the formula (4), in which the definitions of the symbols are as defined above, in a solvent having no reactive hydrogen atom similarly as in step (a) above in the presence of a condensing agent to produce a compound of the above formula (1) wherein $R_3$ is $-NH-(-CH_2)_{\overline{n}}R_5$, in which the definitions of the symbols are as defined above.

The condensing agent mentioned here refers to any condensing agent capable of condensing a carboxyl group with an amino group, as exemplified by N,N'-dicyclohexylcarbodiimide, 1-ethyl-3-(3-dimethylaminopropyl)carbodiimide hydrochloride, 1-ethoxycarbonyl-2-ethoxy-1,2-dihydroquinoline or N,N'-disucciimidylcarbonate.

Use of Compound/Carcinostatic Agent

As is apparent from the physiological experiments set forth hereinafter, the bile acid derivatives according to the present invention have carcinostatic activity and yet are of low toxicity, and therefore these compounds can be useful as carcinostatic agents.

That is, the carcinostatic agent as an embodiment of the present invention comprises a bile acid derivative represented by the above formula (1) or its salt as the active ingredient.

The carcinostatic agent comprises any of the above bile acid derivatives alone or a mixture thereof or a mixture thereof with a liquid or solid auxiliary component in preparation such as an excipient, binder or diluent, which agent can be administered orally or parenterally in any desired preparation form such as powder, granule, tablet, capsule or injection.

Furthermore, if desired, it can be also formulated with any other carcinostatic agent (e.g., 5-FU, mytomycin or crestine). The dose, which may be suitably increased or decreased depending on the age, the body weight or the condition of disease, is ordinarily and desirably 10 mg to 10 g as the bile acid derivative for oral administration for a human adult per day. A preferable example comprises the bile acid derivative and an auxiliary component in preparation. Another preferable example of the present invention is in a unit dosage form for one administration or several divided administrations of the above dose per day.

EXAMPLES

Synthesis of Compound

In the following Examples, the end products synthesized were obtained as colorless powder by evaporation of the solvent used except for those which were crystallized for measurement of the melting points which are shown therein. The symbols and physical and chemical properties of the end products are as shown in the above Table 1.

EXAMPLE 1

Methyl 3-O-[bis(2-chloroethyl)aminocarbonyl] cholate (CA-Me-NM)

To a solution of 8.5 g of methyl cholate dissolved in 20 ml of methylene chloride was added 2.5 g of triethylamine, and 20 ml of a benzene solution containing 2.4 g of phosgene was added dropwise thereto under stirring, and the stirring was continued for 2 hours. Separately, to an ice-cooled solution of 4.7 g of bis(2-chloroethylamine) hydrochloride dissolved in 5 ml of water was added an ice-cooled solution of 1.8 g of potassium hydroxide dissolved in 5 ml of water, and bis(2-chloroethyl)amine formed as an oily precipitate was extracted with 15 ml of chloroform (×3) and dried over anhydrous magnesium sulfate. A solution prepared by addition of 2.5 g of triethylamine to the thus dried chloroform layer was added to the above reaction mixture of methyl cholate and phosgene, and the resultant mixture was stirred at room temperature overnight. Then, the reaction mixture was washed successively with water, 0.5 N hydrochloric acid and water, dried over anhydrous magnesium sulfate, after which the solvent was evaporated. The reaction mixture obtained was purified by silica gel chromatography to obtain 4.8 g of the title compound (yield 40%).

EXAMPLE 2

Ethyl 3-O[bis(2-chloroethyl)aminocarbonyl] cholate (CA-ET-NM)

With the use of 8.6 g of ethyl cholate as the starting material in a reaction similar to that in Example 1, 5.3 g of the title compound was obtained (yield 44%).

EXAMPLE 3

Benzyl 3-O-[bis(2-chloroethyl)aminocarbonyl] cholate (CA-Bz-NM)

With the use of 9.8 g of benzyl cholate as the starting material in a reaction similar to that in Example 1, 5.7 g of the title compound was obtained (yield 43%).

EXAMPLE 4

Methyl 3-O-[bis(2-chloroethyl)aminocarbonyl] deoxycholate (DCA-Me-NM)

With the use of 9.6 g of methyl deoxycholate as the starting material in a reaction similar to that in Example 1, 4.2 g of the title compound was obtained (yield 37%).

EXAMPLE 5

Benzyl 3-O-[bis(2-chloroethyl)aminocarbonyl] ursodeoxycholate (UDCA-Bz-NM)

9.6 g of benzyl ursodeoxycholate, 7.6 g of N,N'-disucciimidyl carbonate and 4 g of triethylamine were added to 20 ml of acetonitrile, and the mixture was stirred at room temperature for 8 hours. Then, a solution of 20 ml of acetonitrile containing 10 g of bis(2-chloroethyl)amine hydrochloride and 5 g of triethylamine was added thereto, and the mixture was stirred at room temperature overnight. Then, 50 ml of ethyl acetate was added, and the resultant mixture was washed successively with water, 2% aqueous sodium hydrogencarbonate solution and water, and dried over anhydrous magnesium sulfate, after which evaporation of the solvent was carried out. The reaction mixture obtained was purified by silica gel chromatography to obtain 5.3 g of the title compound (yield 41%).

EXAMPLE 6

Benzyl 3-O-[bis(2-chloroethyl)aminocarbonyl] chenodeoxycholate (CDCA-Bz-NM)

With the use of 9.6 g of benzyl chenodeoxycholate as the starting material in a reaction similar to that in Example 5, 6.4 g of the title compound was obtained (yield 50%).

EXAMPLE 7

Benzyl 3-O-[bis(2-chloroethyl)aminocarbonyl] lithocholate (LCA-Bz-NM)

With the use of 9.4 g of benzyl lithocholate as the starting material in a reaction similar to that in Example 1, 4.9 g of the title compound was obtained (yield 39%).

EXAMPLE 8

Benzyl 3-O-(2-chloroethylaminocarbonyl) cholate (CA-Bz-CEA)

According to the reaction similar to that in Example 5 except for the use of 10 g of benzyl cholate as the starting material and 6 g of 2-chloroethylamine hydrochloride in place of bis(2-chloroethyl)amine hydrochloride, 6 g of the title compound was obtained (yield 49%).

EXAMPLE 9

Benzyl 3-O-(2-chloroethylaminocarbonyl) deoxycholate (DCA-Bz-CEA)

According to the reaction similar to that in Example 1 except for the use of 9.7 g of benzyl deoxycholate as the starting material and 3 g of 2-chloroethylamine hydrochloride in place of bis(2-chloroethyl)amine hydrochloride, 5.3 g of the title compound was obtained (yield 45%).

EXAMPLE 10

Benzyl 3-O-[bis(2-chloroethyl)aminocarbonyl] ursodeoxycholate (UDCA-Bz-CEA)

With the use of 9.7 g of benzyl ursodeoxycholate as the starting material in a reaction similar to that in Example 8, 4 g of the title compound was obtained (yield 34%).

EXAMPLE 11

Benzyl 3-O-(2-bromoethylaminocarbonyl) deoxycholate (DCA-Bz-BEA)

According to the reaction similar to that in Example 5 except for the use of 9.7 g of benzyl deoxycholate as the starting material and 10 g of 2-bromoethylamine hydrobromide in place of bis(2-chloroethyl)amine hydrochloride, 4.5 g of the title compound was obtained (yield 36%).

EXAMPLE 12

Benzyl 3-O-[bis(2-bromoethyl)aminocarbonyl] ursodeoxycholate (UDCA-Bz-BEA)

With the use of 9.7 g of benzyl ursodeoxycholate as the starting material in a reaction similar to that in Example 11, 3.8 g of the title compound was obtained (yield 30%).

EXAMPLE 13

Benzyl 3-O-[bis(2-bromoethyl)aminocarbonyl] cholate (CA-Bz-BBEA)

According to the reaction similar to that in Example 5 except for the use of 9.8 g of benzyl cholate as the starting material and 15 g of bis(2-bromoethyl)ammonium tosylate in place of bis(2-chloroethyl)amine hydrochloride, 2.6 g of the title compound was obtained (yield 17%).

EXAMPLE 14

3-O-[bis(2-chloroethyl)aminocarbonyl cholic acid (CA-NM)

A solution of 5.9 g of methyl 3-O-[bis(2-chloroethyl)aminocarbonyl] cholate dissolved in a mixture of 10 ml of a 10% (w/v) aqueous sodium hydroxide solution and 50 ml of ethanol was left standing at room temperature for 3 hours. Then 100 ml of ethyl acetate was added, and the resultant mixture was successively washed with 0.5N hydrochloric acid (×1) and water (×3) and dried over anhydrous magnesium sulfate, after which the solvent was evaporated, to obtain 5.5 g of the title compound (yield 96%). The crystallized product formed by addition of chloroform was found to have a melting point of 165° to 166° C.

EXAMPLE 15

3-O-[bis(2-chloroethyl)aminocarbonyl] deoxycholic acid (DCA-NM)

With the use of 5.7 g of methyl 3-O-[bis(2-chloroethyl)aminocarbonyl] deoxycholate as the starting material in a reaction carried out as in Example 14, 5.5 g of the title compound (yield 99%) was obtained. The crystallized product formed by addition of acetonitrile was found to have a melting point of 141° to 143° C.

EXAMPLE 16

3-O-[bis(2-chloroethyl)aminocarbonyl] ursodeoxycholic acid (UDCA-NM)

With the use of 6.5 g of benzyl 3-O-[bis(2-chloroethyl)aminocarbonyl] ursodeoxycholate as the starting material, a reaction was carried out as in Example 14. After completion of the reaction, most of the ethanol in the reaction mixture was evaporated under reduced pressure, then 70 ml of water was added. The resultant solution was washed twice with benzene. After the aqueous solution was made acidic (pH 2) with conc. hydrochloric acid, the solution was extracted with 80 ml of ethyl acetate, and the ethyl acetate layer was washed twice with water and dried over anhydrous magnesium sulfate. Then the solvent was evaporated to produce 5.2 g of the title compound (yield 93%).

EXAMPLE 17

3-O-[bis(2-chloroethyl)aminocarbonyl] chenodeoxycholic acid (CDCA-NM)

To a solution of 6.5 g of benzyl 3-O-[bis(2-chloroethyl)aminocarbonyl] chenodeoxycholate dissolved in 50 ml of tetrahydrofuran was added 0.5 g of 5% palladium on carbon, and hydrogenation was carried out until the starting material disappeared. After completion of the reaction, the catalyst was filtered off, and the filtrate evaporated to produce 5.5 g of the title compound (yield 98%).

EXAMPLE 18

3-O-[bis(2-chloroethyl)aminocarbonyl] lithocholic acid (LCA-NM)

With the use of 6.3 g of benzyl 3-O-[bis(2-chloroethyl)aminocarbonyl] lithocholate as the starting material, a reaction was carried out as in Example 17 to obtain 5.4 g of the title compound (yield 100%). The crystallized product formed by addition of chloroform was found to have a melting point of 158° to 162° C.

EXAMPLE 19

3-O-(2-chloroethylaminocarbonyl)cholic acid (CA-CEA)

With the use of 6.3 g of benzyl 3-O-(2-chloroethylaminocarbonyl) cholate as the starting material, a reaction was carried out as in Example 16 to produce 5 g of the title compound (yield 100%). The crystallized product formed by addition of chloroform was found to have a melting point of 162° to 165° C.

EXAMPLE 20

3-O-(2-chloroethylaminocarbonyl)deoxycholic acid (DCA-CEA)

With the use of 5.9 g of benzyl 3-O-(2-chloroethylaminocarbonyl) deoxycholate as the starting material, a reaction was carried out as in Example 17 to produce 4.9 g of the title compound (yield 98%).

EXAMPLE 21

3-O-(2-chloroethylaminocarbonyl)ursodeoxycholic acid (UDCA-CEA)

With the use of 5.9 g of benzyl 3-O-(2-chloroethylaminocarbonyl) ursodeoxycholate as the starting material, a reaction was carried out as in Example 17 to produce 4.9 g of the title compound (yield 98%).

EXAMPLE 22

3-O-(2-bromoethylaminocarbonyl)deoxycholic acid (DCA-BEA)

With the use of 6.3 g of benzyl 3-O-(2-bromoethylaminocarbonyl) deoxycholate as the starting material, a reaction was carried out as in Example 17 to produce 5.3 g of the title compound (yield 98%).

EXAMPLE 23

3-O-(2-bromoethylaminocarbonyL)ursodeoxycholic acid (UDCA-BEA)

With the use of 6.3 g of benzyl 3-O-(2-bromoethylaminocarbonyl) ursodeoxycholate as the starting material, a reaction was carried out as in Example 17 to produce 5.3 g of the title compound (yield 98%).

EXAMPLE 24

3-O-[bis(2-bromoethyl)aminocarbonyl]cholic acid (CA-BBEA)

With the use of 760 mg of benzyl 3-O-[bis(2-bromoethyl)aminocarbonyl] cholate as the starting material, a reaction was carried out similarly as in Example 17 on 1/10 scale to produce 660 mg of the title compound (yield 99%).

EXAMPLE 25

3-O-[bis(2-chloroethyl)aminocarbonyl]taurocholic acid (CA-Tau-NM)

1.2 g of 3-O-[bis(2-chloroethyl)aminocarbonyl]cholic acid, 700 mg of 1-ethoxycarbonyl-2-ethoxy-1,2-dihydroquinoline, 0.36 ml of triethylamine and 280 mg of taurine were added to 4 ml of dimethylformamide, and reaction was carried out at 90° C. for 1.5 hours. After it was cooled to room temperature, the reaction mixture was added to 100 ml of diisopropyl ether, and the oily precipitate formed was added to 50 ml of ethyl acetate. After washing with 1N hydrochloric acid, the product was dried over anhydrous magensium sulfate, and the solvent was evaporated. The reaction mixture obtained was purified by silica gel chromatography to produce 940 mg of the title compound (yield 66%).

EXAMPLE 26

3-O-[bis(2-chloroethyl)aminocarbonyl]glycocholic acid (CA-Gly-NM)

5.8 g of 3-O-[bis(2-chloroethyl)aminocarbonyl]cholic acid, 1 g of glycine and 2.5 g of dicyclohexylcarbodiimide were added to 150 ml of ethyl acetate and the mixture was refluxed under heating overnight and then cooled to room temperature. Then, filtration of the insolubles was carried out. The filtrate was washed with 0.2N hydrochloric acid, dried over anhydrous magnesium sulfate, and the solvent was evaporated. The reaction mixture obtained was purified by silica gel chromatography to produce 4.2 g of the title compound (yield 66%). The crystallized product formed by addition of chloroform was found to have a melting point of 125° to 127° C.

EXAMPLE 27

3-O-(2-chloroethylaminocarbonyL)glycocholic acid (CA-Gly-CEA)

With the use of 5.1 g of 3-O-(2-chloroethylaminocarbonyl)cholic acid as the starting material, a reaction was carried out as in Example 26 to produce 3.5 g of the title compound (yield 62%).

Physiological Activity

In order to see the DNA synthesis inhibitory effect against cancer cells of the bile acid derivative CA-NM of the present invention (see the above Table 1, Compound No. 14) and its toxicity, biological tests using cultured cells and acute toxicity tests using mice were conducted. The results are given below together with the experimental methods.

DNA Synthesis Inhibitory Effect Against Cancer Cells

A cell suspension of Yoshida ascite hepatoma, AH130, which was subjected to a passage transplantation carried out intraperitoneally in Donryu-strain rat was prepared to a cell density of about $10^6$/ml in the 199 medium (see the textbook "Tissue Culture", published by Asakura Shoten, Tokyo, Japan, 1976) containing 10% fetal bovine serum, $10^{-7}$M insulin, 100 units/ml of penicillin and 100 μg/ml of streptomycin, and each 5 ml of aliquots were apportioned into flasks for tissue culture (culture area 24 cm$^2$) and pre-cultured in a carbon dioxide incubator (5% $CO_2$-95% air, 37° C.) for 24 hours. After the cultivation, the cells were collected by centrifugation (1,000 rotations/min., 5 min.) to prepare a cell suspension to a cell density of $2.4 \times 10^5$/ml. After 1 ml each of aliquots of the suspension was apportioned into each well of a 24 wells-type tissue culture plate (culture area 1.9 cm$^2$/well), by use of CA-NM (see the above Table 1, Compound No. 14), the prostate carcinostatic agent NITROMIN ® (supplied by Yoshitomi Seiyaku, Tokyo, Japan) and cholic acid (control) all prepared to 100-fold concentration of the final concentration, the culture fluids were prepared to final concentrations of 0.5 μM, 5 μM and 50 μM, respectively, and each preparation was cultured for 2 hours.

After the cultivation, a solution containing thymidine labelled with tritium was added to a radioactivity of 0.25 μCi/ml in the medium, and the cultivation was further carried out for 22 hours. After completion of the cultivation, the cells in each well were collected by centrifugation, washed twice with ice-cooled PBS(−) solution (supplied by Nissui Seiyaku, Tokyo, Japan), and then treated with 10% and 5% ice-cooled trichloroacetic acid, in order.

Then, after washing once with alcohol, the cells from each well were treated with 0.25 ml of 1N sodium hydroxide and the mixture was warmed at 52° C. for 1 hour. After being cooled to room temperature, the mixture was neutralized with 0.25 ml of 1N hydrochloric acid and transferred into a vial for liquid scintillation, and, with addition of 5 ml of cocktail for liquid scintillation (ACS-II, Amersham, Ill., USA), radioactivity of tritium in the vial was measured by a liquid scintillation counter.

The results are as shown in the following Table.

TABLE 2

| Test sample | Concentration (μM) | Radioactivity (%) |
|---|---|---|
| CA-NM | 0.5 | 64.5 |
|  | 5 | 44.1 |
|  | 50 | 23.3 |
| NITROMIN ® | 0.5 | 111.7 |
| (supplied by Yoshitomi | 5 | 57.5 |
| Seiyaku, Tokyo, Japan) | 50 | 3.2 |

The radioactivity (%) in Table 2 is shown in terms of percentage of radioactivity when the radioactivity of the control group (cholic acid) is made 100.

From these results, the bile acid derivatives CA-NM of the present invention was confirmed to have a DNA synthesis inhibitory effect against cancer cells to the same extent as compared with the already existing carcinostatic agent NITROMIN®, and its effect was found to be dose-dependent.

Toxicity

As for toxicity, 10 g/kg of CA-NM of the present invention was administered orally once to ddY-strain mice (9 mice per one group), and its acute toxicity was observed. As a result, no mortality case was observed 30 days after administration, and therefore the bile acid derivatives of the present invention can be said to be generally of low toxicity.

We claim:

1. A bile acid derivative represented by the following formula (1) and its salt:

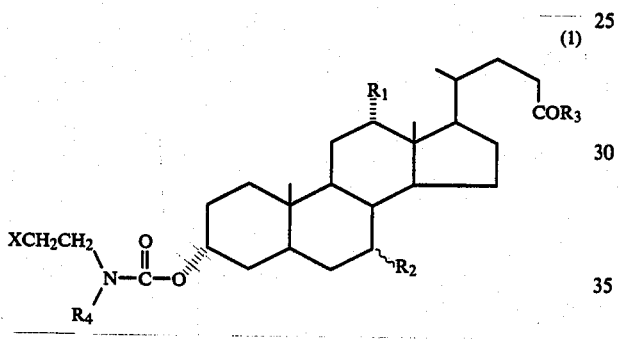

wherein each of $R_1$ and $R_2$ is a hydrogen atom or a hydroxyl group, $R_3$ is a benzyloxy group or $-NH(CH_2)_nR_5$ (wherein $R_5$ is a carboxyl group or sulfonyl group, and n represents the integer of 1 or 2), X is a halogen atom, $R_4$ is a hydrogen atom or $XCH_2CH_2-$, ﹙﹚ is an α-bond, and ∼∼∼ is an α- or β-bond.

2. The bile acid derivative of claim 1, wherein $R_3$ is a benzyloxyl group.

3. The bile acid derivative of claim 1, wherein $R_3$ is $-NH(CH_2)_nR_5$ (wherein $R_5$ is a carboxyl group or sulfonyl group, and n represents the integer 1 or 2).

4. The bile acid derivative of claim 1, wherein $R_4$ is a hydrogen atom.

5. The bile acid derivative of claim 1, wherein $R_4$ is $XCH_2CH_2-$, wherein X is a halogen atom.

6. A process for producing a bile acid derivative represented by the following formula:

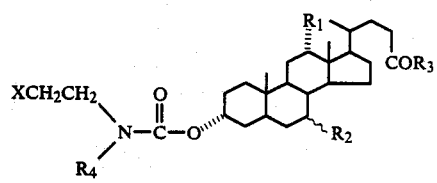

wherein each of $R_1$ and $R_2$ is a hydrogen atom or a hydroxyl group, $R_3$ is $-NH(CH_2)_nR_5$ (wherein $R_5$ is a carboxyl group or sulfonyl group, and n represents the integer of 1 or 2), X is a halogen atom, $R_4$ is a hydrogen atom or $XCH_2CH_2-$, ﹙﹚ is an α-bond, and ∼∼∼ is an α- or β-bond, comprising the steps (a), (b), (c) and (d) described below:

(a) causing an active carbonation reagent to react with a bile acid derivative represented by the formula (2):

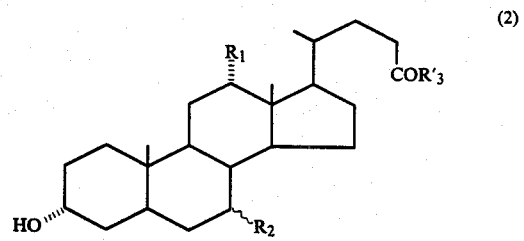

wherein each of $R_1$ and $R_2$ is a hydrogen atom or a hydroxyl group, $R'_3$ is a lower alkoxyl group or benzyloxy group, ﹙﹚ is an α-bond, and ∼∼∼ is an α- or β-bond;

(b) causing a compound represented by the formula (3):

wherein X is a halogen atom, and $R_4$ is a hydrogen atom or $XCH_2CH_2-$, to react with the active carbonated product obtained;

(c) subjecting the bile acid derivative obtained in the above steps (a) and (b) to hydrolysis; and (d) causing the above hydrolyzate to react with a compound represented by the formula (4):

$$H_2N(CH_2)_nR_5 \qquad (4)$$

wherein $R_5$ is a carboxyl group or sulfonyl group, and n represents the integer of 1 or 2, in the presence of a condensing agent.

* * * * *